United States Patent [19]

Tsumura et al.

[11] Patent Number: 5,783,721
[45] Date of Patent: Jul. 21, 1998

[54] PREPARATION OF SILANES

[75] Inventors: Hiroshi Tsumura, Annaka; Tetsuo Nakanishi, Usui-gun; Hiroshi Nakayama; Yukinori Satoh, both of Annaka, all of Japan

[73] Assignee: Shin-Etsu Chemical Co., Ltd., Japan

[21] Appl. No.: 781,209

[22] Filed: Jan. 10, 1997

[30] Foreign Application Priority Data

Jan. 12, 1996 [JP] Japan ................... 8-022112

[51] Int. Cl.$^6$ .................... C07F 7/16
[52] U.S. Cl. .................... 556/472; 423/342
[58] Field of Search .................. 556/472; 423/342

[56] References Cited

U.S. PATENT DOCUMENTS

| | | |
|---|---|---|
| 4,218,387 | 8/1980 | Maas et al. |
| 4,450,282 | 5/1984 | Ritzer et al. ............ 556/472 |
| 4,554,370 | 11/1985 | Ward, III et al. |
| 4,895,969 | 1/1990 | Feldner et al. ............ 556/472 |
| 5,015,751 | 5/1991 | Feldner et al. |
| 5,250,716 | 10/1993 | Mui ............ 556/472 |
| 5,312,948 | 5/1994 | Freeburne et al. ............ 556/472 |
| 5,380,903 | 1/1995 | Degen et al. ............ 556/472 |

FOREIGN PATENT DOCUMENTS

| | | |
|---|---|---|
| 223 447 | 5/1987 | European Pat. Off. |
| 647 646 | 12/1995 | European Pat. Off. |

*Primary Examiner*—Paul F. Shaver
*Attorney, Agent, or Firm*—Millen, White, Zelano & Branigan, P.C.

[57] ABSTRACT

An (alkylhalo)silane is prepared by charging a reactor with a contact mass comprising metallic silicon powder and a copper catalyst and feeding a gas containing an alkyl halide into the reactor whereby the silane is formed by direct synthesis. The contact mass in the reactor during reaction consists of particles having a mean particle size of 5–150 μm and containing 10–80% by weight of particles having a particle size of up to 30 μm and 10–90% by weight of particles having a particle size of at least 90 μm. The contact mass is well fluidized to ensure rapid and uniform reaction whereby the (alkylhalo)silane is prepared at high selectivity with a minimized elutriating loss of contact mass.

14 Claims, 1 Drawing Sheet

PREPARATION OF SILANES

BACKGROUND OF THE INVENTION

1. Field of the Invention

This invention relates to an improvement in the direct process for preparing (alkylhalo)silanes from metallic silicon and alkyl halides, the process being capable of effecting rapid uniform reaction therebetween and forming the end product of quality at high selectivity in high yields.

2. Prior Art

With respect to the synthesis of alkylhalosilanes, Rochow first disclosed in U.S. Pat. No. 2,380,995 direct synthesis reaction between metallic silicon and an alkyl halide in the presence of a copper catalyst. Since then, there have been reported a number of research works relating to various co-catalysts used in the presence of copper catalyst, various copper catalysts and treatment thereof, reactors, additives to be added during reaction, and the like.

The direct synthesis process involves activating a contact mass comprising metallic silicon and copper catalyst and introducing an alkyl halide into the activated contact mass for accomplishing gas-solid direct contact between the metallic silicon and the alkyl halide, thereby producing an alkylhalosilane. Fluidized bed reactors are generally used for such commercial synthesis of alkylhalosilanes.

In the direct synthesis process, however, if a uniformly fluidized state is not available within the fluidized bed reactor, the production rate of alkylhalosilane can have a distribution in the reactor and the rate of heat removal from within the system ceases to be even within the reactor. As a result, sintering and segregation of catalyst particles in the contact mass and development of hot spots higher than the average temperature in the reactor are likely to occur. These factors induce deactivation of the catalyst, decomposition of the alkyl halide feed and alkylhalosilane product, accumulation of impurity carbon, aggravation of selectivity and lowering of yield. Because of these problems, continuous operation for a long term becomes difficult. There also arises the disadvantage that a zone in the reactor where the rate of formation of alkylhalosilane is locally retarded can reduce the overall rate of formation of alkylhalosilane in the entire reactor.

In establishing uniform fluidization, the particle size and particle size distribution of contact mass particles are crucial factors. In general, a contact mass with a smaller mean particle size tends to create poor fluidization because smaller particles tend to agglomerate or give rise to a channeling phenomenon.

According to Kunii and Levenspiel "Fluidization Engineering" (Second Edition), 1991, particles with a size of less than about 30 μm are classified into a particle group assigned "Geldart C" and regarded especially difficult to fluidize because of higher intergranular forces. Because of a low terminal velocity, fine particles are likely to be elutriated and carried by gas introduced into the fluidized bed. As a consequence, the effective utilization of the contact mass for reaction can be reduced and a dust collecting capacity must be enhanced for collecting the elutriated contact mass.

JP-A 120391/1987 discloses a reactor charge of metallic silicon powder having a mean particle size within the range of 0.1 to 800 μm, preferably 0.1 to 150 μm. Even within this mean particle size range, use of relatively small metallic silicon particles having a mean particle size of less than 30 μm cannot avoid the above-mentioned disadvantages.

Freeburne et al. U.S. Pat. No. 5,312,948 discloses a process using metallic silicon particles having a size within the range of 1 to 85 μm and a particle size mass distribution characterized by a 10th percentile of 2.1 to 6 μm, a 50th percentile of 10 to 25 μm, and a 90th percentile of 30 to 60 μm. Silicon particles having such a small particle size also suffer from disadvantages including poor fluidization and low utilization as mentioned above.

In order to obtain relatively good fluidization, it was thus believed desirable that the metallic silicon powder in the reactor have a mean particle size of greater than 30 μm. It is described in JP-A 209892/1990 that the metallic silicon powder used in the synthesis of alkylhalosilanes should preferably have a mean particle size of up to 1,000 μm, especially up to 500 μm and that for a mean particle size of 100 to 150 μm, use of metallic silicon powder having a particle size distribution between 30 μm and 300 μm is preferred.

Also JP-B 5396/1991 describes it preferable that silicon in the fluidized bed have a particle size of less than 700 μm and a mean particle size of 20 to 300 μm, and silicon particles have an average diameter of 100 to 150 μm.

When consideration is made from the aspect of reaction, however, metallic silicon powder having a smaller particle size is generally preferred as opposed to the aspect of obtaining good fluidization. This is because a smaller particle size improves heat transfer between particles and particles participating in reaction have a large surface area so that reaction becomes rapid and uniform. Therefore, if metallic silicon powder to be fed or metallic silicon powder charged in the reactor consists of particles having a mean particle size in excess of 100 μm and free of fine particles, it is impossible to carry out the reaction rapidly and uniformly until a satisfactory level, which is disadvantageous in production efficiency.

Moreover, metallic silicon powder is generally obtained by crushing a grain of metallic silicon. Thus metallic silicon powder immediately after crushing contains many fine particles having a particle size of less than 30 μm. The step of separating such fine particles by means of a screen or the like is disadvantageous not only in commercial manufacture, but also from the standpoints of effective utilization of fine particles and resource saving.

Therefore, it is a commercially important task to find a compromise between the two disadvantages mentioned above, that is, to prepare alkylhalosilanes by a process capable of ensuring both good fluidization of the contact mass and rapid and uniform progress of reaction.

SUMMARY OF THE INVENTION

An object of the present invention is to provide a process for preparing an (alkylhalo)silane of quality in a commercially advantageous manner by effecting rapid and uniform reaction while ensuring good fluidization of the contact mass, maintaining high selectivity of the (alkylhalo)silane, and minimizing a loss of the contact mass by elutriating.

In connection with the process wherein an (alkylhalo) silane is prepared by charging a reactor with a contact mass comprising metallic silicon powder and a copper catalyst and feeding a reactant gas containing an alkyl halide into the reactor whereby the (alkylhalo)silane is formed by direct synthesis, we have found that better results are obtained when the contact mass in the reactor during the progress of reaction is adjusted so as to consist of particles having a mean particle size of up to 150 μm, containing at least 10% by weight of a fraction of particles having a particle size of up to 30 μm and containing a fraction of particles having a particle size of at least 90 μm. That is, the commercially advantageous direct process is employable. the particles in the reactor can be maintained well fluidized during the progress of reaction, metallic silicon powder having a small particle size can be used as a raw material, rapid and uniform reaction takes place, the selectivity of a dialkyldihalosilane is high, a loss of the contact mass by elutriating is minimized, and therefore the contact mass can be effectively utilized. A dust collector may not be required. Then the dialkyldihalosilane of quality is produced in high yields.

Accordingly, the present invention provides a process for preparing a silane of the general formula (I):

$$R_nSiX_{4-n} \quad (I)$$

wherein R is a lower alkyl group having 1 to 4 carbon atoms, X is a halogen atom, and letter n is an integer of 0 to 4, comprising the steps of charging a reactor with a contact mass comprising metallic silicon powder and a copper catalyst, and feeding a reactant gas containing an alkyl halide into the reactor whereby the silane is formed by direct synthesis, characterized in that the contact mass in the reactor during the progress of reaction consists of particles having a mean particle size of up to 150 μm and containing at least 10% by weight of a fraction of particles having a particle size of up to 30 μm and a fraction of particles having a particle size of at least 90 μm.

In one preferred embodiment, the process further involves the steps of monitoring the mean particle size and particle size distribution of the contact mass in the reactor during the progress of reaction and replenishing metallic silicon powder or contact mass of such a particle size that the mean particle size and particle size distribution of the resulting contact mass in the reactor may fall within the above-defined range.

BRIEF DESCRIPTION OF THE DRAWINGS

These and further features of the present invention will be apparent with reference to the following description and drawings, wherein.

the only figure.

DESCRIPTION OF THE PREFERRED EMBODIMENT

Figure 1:
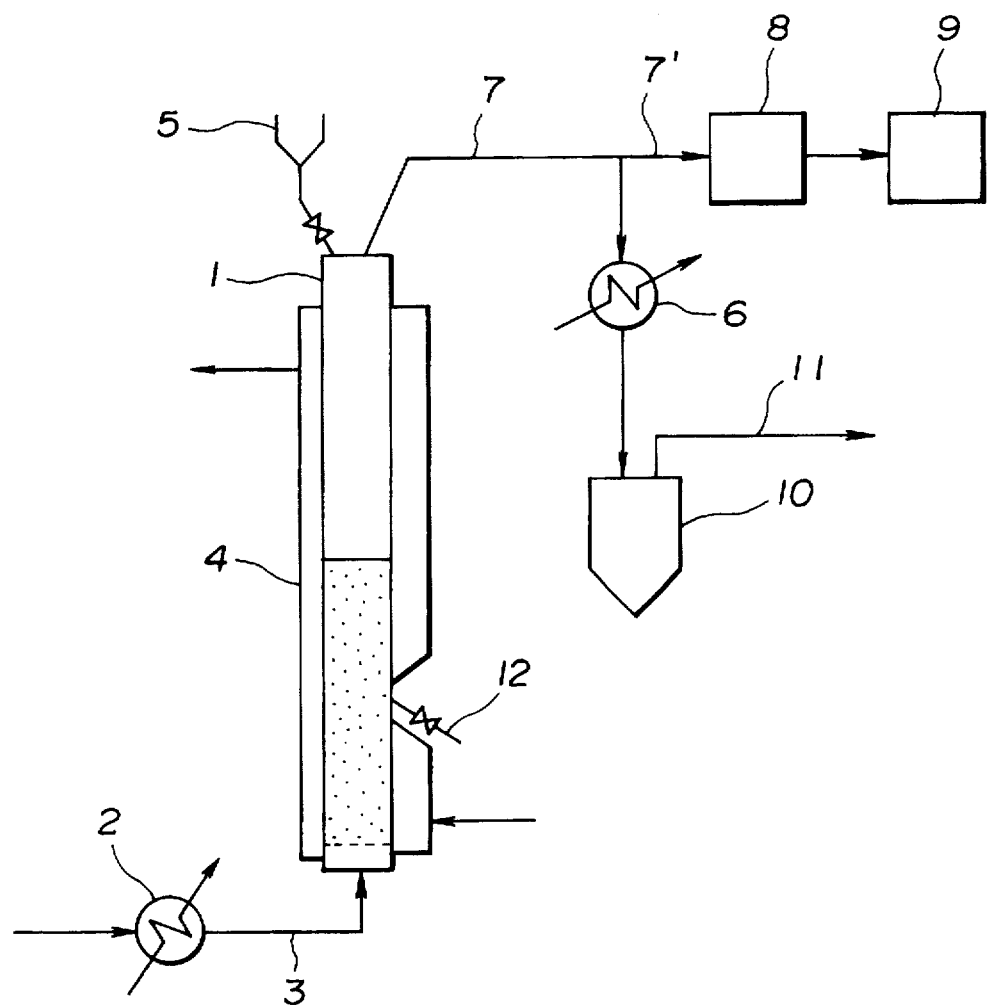
FIG. 1 is a schematic view showing a silane preparing system for use in the practice of the present process.

Briefly stated, the process of the present invention is to prepare an (alkylhalo)silane through direct synthesis from metallic silicon powder and an alkyl halide in the presence of a copper catalyst. The reactor used in the preparation of (alkylhalo)silane by the process of the invention may be any of well-known reactors including fluidized bed reactors and agitation type reactors. Use of fluidized bed reactors is preferred for commercial manufacture because high yield, selectivity and effective utilization of energy are expected.

The metallic silicon powder used herein is preferably metallurgical silicon with a purity of at least 97% by weight, especially at least 98% by weight.

For the copper catalyst, any form of copper may be used, for example, elemental copper such as fine copper powder and flake copper, copper alloys such as Cu-Zn, Cu-Si, and Cu-Sb, and copper compounds such as cuprous oxide, cupric oxide, and copper halides. The copper catalyst is preferably used in an amount of about 1 to 10 parts, especially about 2 to 8 parts by weight of copper per 100 parts by weight of the metallic silicon powder.

As is well known in the art, a promoter such as zinc, antimony and tin may be used along with the copper catalyst. The promoter may be added in a conventional amount. Zinc may be added in an amount of 0.05 to 1% by weight for the weight of the metallic silicon powder. Antimony and tin may be added in an amount of 0.01 to 0.1% by weight for the weight of the metallic silicon powder.

Alkyl halides are reacted with metallic silicon to form (alkylhalo)silanes. Exemplary alkyl halides include methyl chloride, ethyl chloride, methyl bromide, and ethyl bromide. Among these, methyl chloride is commercially most useful. Dimethyldichlorosilane prepared using methyl chloride finds numerous applications as a raw material for a variety of silicone polymers.

Desirably the alkyl halide reactant is previously heated and gasified before it is fed into the reactor. The alkyl halide gas may be used alone or in admixture with an inert gas. The inert gas used herein includes helium, argon and nitrogen, with the nitrogen being preferred for economy.

The alkyl halide may be fed in an amount equal to or greater than the theoretical amount necessary to form the end (alkylhalo)silane and at a flow rate (combined with inert gas if any) equal to or greater than the flow rate necessary to fluidize the contact mass in the reactor.

According to the invention, an (alkylhalo)silane of the general formula (I):

$$R_nSiX_{4-n} \quad (I)$$

wherein R is a lower alkyl group having 1 to 4 carbon atoms, X is a halogen atom, and letter n is an integer of 0 to 4 is prepared from the above-mentioned reactants by direct synthesis. In formula (I), R is a lower alkyl group having 1 to 4 carbon atoms, for example, methyl, ethyl, propyl and butyl groups. X is a halogen atom, for example, chloro, bromo and fluoro.

According to the process of the invention, the reactor is charged with a contact mass containing metallic silicon powder and a copper catalyst, all as defined above. Then a reactant gas containing an alkyl halide is introduced into the reactor where an (alkylhalo)silane of formula (I) is formed through direct synthesis. During the progress of reaction, the contact mass in the reactor is adjusted so as to consist of particles having a mean particle size of up to 150 μm and containing at least 10% by weight of a fraction of particles having a particle size of up to 30 μm and a fraction of particles having a particle size of at least 90 μm.

More specifically, the contact mass particles in the reactor during reaction should be adjusted so as to have a mean particle size of up to 150 μm, preferably 5 to 80 μm. Preferably the mean particle size is kept constant within ±10% of the preset value. If the mean particle size of contact mass exceeds 150 μm, uniform fluidization is easily established, but larger particle sizes aggravate heat transfer between particles, failing to drive rapid and uniform reaction to a satisfactory extent.

It is noted that the mean particle size of metallic silicon powder indicates a median diameter known as $d_{P50}$ corresponding to 50% on a volume basis cumulative distribution curve of metallic silicon powder.

In the fluidized bed reactor during reaction, the contact mass particles should contain at least 10%, preferably 20 to 80% by weight of a fraction of particles having a particle size of up to 30 μm. The contact mass should also contain a fraction of particles having a particle size of at least 90 μm, preferably in an amount of 10 to 90% by weight, more preferably 20 to 50% by weight. If the content of the fraction of particles of 30 μm or less is less than 10% by weight, there are available fewer fine particles which participate in reaction, have a large surface area, and ensure good heat transfer, so that the reaction rate becomes slower and reaction becomes non-uniform, leading to lower selectivity. If the contact mass is free of particles having a particle size of at least 90 μm, particle agglomeration and channeling phenomenon are likely to occur to exacerbate the fluidized state, resulting in operational drawbacks including a shorter catalyst lifetime, lower selectivity of dialkyldihalosilane, and a loss of the contact mass by elutriating.

The adjustment of mean particle size and particle size distribution of the contact mass can be done mainly by milling the raw material or metallic silicon powder in a controlled manner. To this end, various milling machines such as roller mills, sand mills and ball mills may be used.

By monitoring the mean particle size and particle size distribution of the contact mass in the reactor during steady reaction and feeding into the reactor a metallic silicon powder or contact mass having a specific mean particle size and particle size distribution as determined from the monitoring results, the mean particle size and particle size distribution of the contact mass in the reactor during steady reaction can be controlled so as to fall within the above-defined range. That is, by feeding and blending a fraction of metallic silicon particles or contact mass particles having a certain mean particle size and particle size distribution (or plural fractions of metallic silicon particles or contact mass particles having different mean particle sizes and particle size distributions) into the reactor during steady reaction, adjustment is done such that the combined contact mass may have a mean particle size and particle size distribution within the range of the invention. In the embodiment wherein this monitoring/replenishing process is employed, if there are furnished two or three fractions of metallic silicon particles or contact mass particles having different mean particle sizes and particle size distributions, a contact mass having a desired mean particle size and particle size distribution is readily obtained therefrom. The troublesome step of adjusting the raw material is then eliminated.

In the process of the invention, reaction takes place under the same conditions as in the well-known processes, for example, at a temperature of 250° to 350° C., especially 280° to 300° C. and a pressure of 0 to 10 atm.

There has been described an (alkylhalo)silane preparing process capable of producing an (alkylhalo)silane of quality in high yields, at a high utilization of the contact mass and in a commercially advantageous manner by effecting rapid and uniform reaction while ensuring good fluidization of the contact mass, maintaining high selectivity of the alkylhalosilane, especially dialkyldihalosilane and minimizing a loss of the contact mass by elutriating.

EXAMPLE

Examples of the present invention are given below by way of illustration and not by way of limitation. All parts are by weight.

Example 1

A system as shown in FIG. 1 was used for the preparation of an alkylhalosilane. The system includes a fluidized bed type column or reactor 1 having an inner diameter of 80 mm and a height of 1,150 mm. An input line 3 having a preheater 2 is connected to the reactor 1 at the bottom for introducing reactant gas. The reactor 1 is surrounded by a jacket 4 through which a heating medium is circulated for heating the reactor as shown by incoming and outgoing arrows. The reactor 1 is provided at the top with a charging line 5 for charging a contact mass consisting of silicon powder and catalyst to the reactor. The reactor 1 is provided at the top with an output line 7 which includes a cooling trap 6. A sampling branch 7' which is connected to the output line 7 upstream of the trap 6 includes a hot automatic gas sampler 8 and a gas chromatograph 9. The output line 7 leads to a collecting container 10 having an exhaust gas line 11. A line 12 is connected to the reactor 1 for sampling the contact mass.

The reactor 1 was heated to a temperature of 280° C. by circulating the heating medium, typically oil through the jacket 4. Through the line 5, the reactor 1 was charged with a contact mass, that is, 100 parts of metallic silicon powder of commercial grade having a mean particle size of 44 μm and 3 parts of a catalyst mixture of copper, zinc and antimony. Nitrogen gas was introduced into the reactor 1 near the bottom for fluidizing the contact mass at 280° C. for one hour before a gas mixture of methyl chloride and nitrogen preheated by the preheater 2 was introduced into the reactor 1 through the input line 3 at a superficial velocity of 7 cm/sec. to start reaction. Reaction was continued at a temperature of 290° C. The product was delivered to the container 10 along the output line 7 while unreacted methyl chloride and nitrogen were carried over along with the product. The product and unreacted methyl chloride were condensed at the cooling trap 6 and collected in the container 10. Uncondensed nitrogen gas was exhausted through the exhaust line 11. A portion of the product was sampled through the sampling branch 7' to the automatic gas sampler 8 and gas chromatograph 9 where the sample was analyzed by a thermal conductivity detector (TCD).

In order to continue reaction, metallic silicon powder and catalyst mixture were replenished at intervals of 2 hours. The amount of metallic silicon powder replenished corresponded to the amount of silicon consumed for reaction which was calculated from the quantity of the liquid product. At the same time, a sample of the contact mass was taken out through the sampling line 12 and measured for a mean particle size as represented by $d_{P50}$. The mean particle size $d_{P50}$ of the additional contact mass was adjusted based on the measurement of $d_{P50}$ such that the resulting contact mass in the reactor during reaction might have a mean particle size $d_{P50}$ of 60 μm. This adjustment was carried out by properly mixing a first metallic silicon powder portion with $d_{P50}$ of 32 μm and a second metallic silicon powder portion with $d_{P50}$ of 44 μm. By virtue of this adjustment, the particle size distribution of the contact mass in the reactor during steady reaction was maintained at the following proportion and substantially constant.

| Particle size distribution | |
| --- | --- |
| 0–30 μm | 24% |
| 30–90 μm | 36% |
| 90 μm – | 40% |

It is noted that the gas mixture had a methyl chloride concentration of 80% during reaction.

Reaction was stopped by interrupting the supply of methyl chloride gas when a metallic silicon utilization of 50% was reached. The metallic silicon utilization is defined as A/B×100% wherein A is the weight (kg) of metallic silicon consumed for reaction and B is the overall weight (kg) of metallic silicon charged.

The average reaction rate from the start to the end of reaction was 200 g/kg·hr and the product contained 87% by weight of dimethyldichlorosilane and the remainder of methylchlorosilane on the average. The contact mass elutriated from the reactor was 6% based on the weight of the additional contact mass.

Examples 2–5 and Comparative Examples 1–3

The procedure of Example 1 was repeated while varying the mean particle size of contact mass charge, the mean particle size and particle size distribution of contact mass in the reactor during reaction, and the mean particle size of additional contact mass. The average reaction rate from the start to the end of reaction, the average proportion of dimethyldichlorosilane, and the amount of contact mass elutriated from the reactor were measured. The results are shown in Table 1.

TABLE 1

|  |  | E1 | E2 | E3 | E4 | E5 | CE1 | CE2 | CE3 |
|---|---|---|---|---|---|---|---|---|---|
| Mean particle size of contact mass in reactor (μm) | | 60 | 100 | 90 | 40 | 140 | 140 | 15 | 100 |
| Particle size distribution of contact mass in reactor (%) | −30 μm | 24 | 15 | 12 | 45 | 12 | 2 | 69 | 6 |
| | 30–90 μm | 36 | 30 | 38 | 42 | 8 | 23 | 31 | 40 |
| | 90 μm– | 40 | 55 | 50 | 13 | 80 | 75 | 0 | 54 |
| Mean particle size of contact mass charge (μm) | | 44 | 91 | 91 | 32 | 120 | 120 | 15 | 91 |
| Mean particle size of additional contact mass (μm) | | 32 | 44 | 44 | 15 | 15 | 120 | 10 | 91 |
| | | 44 | 91 | | | | | | |
| Average proportion of dimethyldichlorosilane (wt %) | | 87 | 85 | 86 | 88 | 84 | 71 | 75 | 77 |
| Average reaction rate (g-silane/kg-contact mass · hr) | | 200 | 160 | 160 | 240 | 160 | 80 | 240 | 100 |
| Elutriating loss of contact mass (%) | | 6 | 4 | 5 | 9 | 3 | 1 | 21 | 3 |

It is noted that the elutriating loss of contact mass was calculated as C/D×100% wherein C is the weight (g) of elutriated contact mass and D is the weight (g) of additional contact mass.

It is evident from Table 1 that Comparative Examples 1 to 3 wherein the particle size distribution of contact mass in the reactor during reaction was outside the scope of the invention were low in proportion of dimethyldichlorosilane and/or reaction rate. In particular, Comparative Example 2 wherein the contact mass contained much fine particles had a high reaction rate, but a low average proportion of dimethyldichlorosilane and an extremely increased elutriating loss. In contrast, the process of the invention could produce an alkylhalosilane of quality at a high selectivity through rapid and uniform reaction.

Although some preferred embodiments have been described, many modifications and variations may be made thereto in the light of the above teachings. It is therefore to be understood that within the scope of the appended claims, the invention may be practiced otherwise than as specifically described.

We claim:
1. A process for preparing a silane of the formula (I):

$$R_nSiX_{4-n} \tag{I}$$

wherein R is a lower alkyl group having 1 to 4 carbon atoms, X is a halogen atom, and letter n is an integer of 0 to 4, comprising:

feeding a reactant gas containing an alkyl halide into a reactor containing a contact mass comprising metallic silicon powder and a copper catalyst, whereby the silane is formed by direct synthesis, the contact mass in the reactor during the progress of reaction consisting of particles having a mean particle size of 5 to 80 μm and containing at least 10% by weight of a fraction of particles having a particle size of up to 30 μm and a fraction of particles having a particle size of at least 90 μm.

2. The process of claim 1 further comprising
  monitoring the mean particle size and particle size distribution of the contact mass in the reactor during the progress of reaction, and
  replenishing the metallic silicon powder of the contact mass of a particle size such that the mean particle size and particle size distribution of the resulting contact mass in the reactor is maintained within the range defined in claim 1.

3. The process of claim 1, wherein the contact mass in the reactor during the progress of reaction consists of particles having a mean particle size of 5 to 80 μm and containing at least 10% by weight of a fraction of particles having a particle size of up to 30 μm and 10 to 50% by weight of a fraction of particles having a particle size of at least 90 μm.

4. The process of claim 3, further comprising
  monitoring the mean particle size and particle size distribution of the contact mass in the reactor during the progress of reaction, and
  replenishing the metallic silicon powder or the contact mass of a particle size such that the mean particle size and particle size distribution of the resulting contact mass in the reactor is maintained within the range defined in claim 3.

5. A process according to claim 1, conducted in a fluidization bed reactor.

6. The process of claim 1, wherein the metallic silicon powder is metallurgical silicon with a purity of at least 97%.

7. The process of claim 1, wherein the copper catalyst is elemental copper, copper alloy or a copper compound.

8. The process of claim 1, wherein the copper catalyst is provided in an amount of about 1 to 10 parts by weight of copper per 100 parts by weight of the metallic silicon powder.

9. The process of claim 1, wherein a zinc, antimony or tin promoter is used together with the copper catalyst.

10. The process of claim 1, wherein the alkyl halide is methyl chloride and dimethyldichlorosilane is formed by the direct synthesis.

11. The process of claim 1, wherein the alkyl halide is heated and gasified for the process.

12. The process of claim 1, wherein the contact mass contains 20 to 80% by weight of a fraction of particles having a particle size of up to 30 μm.

13. The process of claim 1, wherein the direct synthesis takes places at a temperature of 250° to 350° C.

14. The process of claim 1, wherein the direct synthesis takes places at a temperature of 280° to 300° C.

* * * * *